(12) United States Patent
Gobezie et al.

(10) Patent No.: US 11,901,061 B2
(45) Date of Patent: Feb. 13, 2024

(54) ADAPTATION OF TELEHEALTH IN PHYSICAL THERAPY

(71) Applicant: PT Genie, LLC, Orlando, FL (US)

(72) Inventors: Reuben Gobezie, Orlando, FL (US); Laurence D. Higgins, Brookline, MA (US)

(73) Assignee: PT GENIE, LLC, Orlando, FL (US)

( * ) Notice: Subject to any disclaimer, the term of this patent is extended or adjusted under 35 U.S.C. 154(b) by 191 days.

(21) Appl. No.: 17/333,658

(22) Filed: May 28, 2021

(65) Prior Publication Data
US 2021/0375426 A1    Dec. 2, 2021

Related U.S. Application Data

(60) Provisional application No. 63/031,969, filed on May 29, 2020.

(51) Int. Cl.
*G16H 20/30* (2018.01)
*A61B 5/00* (2006.01)

(52) U.S. Cl.
CPC ........... *G16H 20/30* (2018.01); *A61B 5/0004* (2013.01); *A61B 5/0077* (2013.01)

(58) Field of Classification Search
CPC ............................... G16H 20/00; G16H 20/30
USPC .......................................................... 705/3
See application file for complete search history.

(56) References Cited

U.S. PATENT DOCUMENTS

| | | |
|---|---|---|
| 8,690,578 B1 | 4/2014 | Nusbaum |
| 9,198,622 B2 | 12/2015 | Kaleal |
| 9,199,122 B2 | 12/2015 | Kaleal |
| 9,501,942 B2 | 11/2016 | Kaleal |
| 9,652,992 B2 | 5/2017 | Kaleal |
| 2003/0046114 A1 | 3/2003 | Davies |

(Continued)

FOREIGN PATENT DOCUMENTS

KR    101602990 B1 *  3/2016

OTHER PUBLICATIONS

Tetzlaff, Amanda; the Effects of a 12-Week, Virtual, A+Home Upper Limb Training Program for Stroke Survivors on Falls Self-Efficacy and Physical Functioning; University of Windsor (Canada), ProQuest Dissertations Publishing, 2021. 28772804. (Year: 2021).*

(Continued)

*Primary Examiner* — Hiep V Nguyen
(74) *Attorney, Agent, or Firm* — TAROLLI, SUNDHEIM, COVELL & TUMMINO L.L.P.

(57) ABSTRACT

Many physical therapy practitioners have not adopted telehealth because of practical, regulatory and/or payor/reimbursement complexities. Systems and methods described herein can facilitate the adaptation of telehealth in physical therapy. A unique first virtual physical therapy session for a first patient (at a first location) using a first instance of a physical therapy system can be conducted by a practitioner (at a location) at a time in a first channel. A a unique second virtual physical therapy appointment for a second patient (at a second location) using a second instance of the physical therapy system can be conducted by the practitioner (at the location) at the time in a second channel. The practitioner monitors the first channel and the second channel during the time in order to coach, correct, and/or counsel the first patient and the second patient.

16 Claims, 14 Drawing Sheets

(56) References Cited

U.S. PATENT DOCUMENTS

2007/0282228 A1* 12/2007 Einav ............... A63B 21/00181
                                                    600/300
2014/0058742 A1   2/2014 Chari

OTHER PUBLICATIONS https://www.softwareadvice.com/medical/nethealth-profile/ last accessed May 28, 2021.

* cited by examiner

ADAPTATION OF TELEHEALTH IN PHYSICAL THERAPY

TECHNICAL FIELD

The present disclosure relates generally to physical therapy and, more specifically, to systems and methods that facilitate the adaptation of telehealth in physical therapy.

BACKGROUND

Generally, telehealth refers to remote healthcare services using electronic information and telecommunication technology. Telehealth can be used by physical therapy practitioners to keep themselves and their patients safe. Many physical therapy practitioners have not adopted telehealth because of practical, regulatory and/or payor/reimbursement complexities.

SUMMARY

Provided herein is a solution that facilitates the adaptation of telehealth in physical therapy. The systems and methods described herein can simplify the practical, regulatory, and/or payor/reimbursement complications for physical therapy practitioners.

In one aspect, the present disclosure can include a system that facilitates the adaptation of telehealth for physical therapy. The system can include a memory that stores instructions and a processor to access the memory and execute the instructions to: conduct a unique first physical therapy session with a first patient by a practitioner at a time on a first channel, wherein the practitioner is at a location and the first patient is at a first location remote from the location, wherein the first patient uses a first instance of a physical therapy system during the first physical therapy session; and conduct a unique second physical therapy session with a second patient by the practitioner at another time on a second channel, wherein the practitioner is at the location and the second patient is at a first location remote from the location and the other time overlaps the time, wherein the second patient uses a second instance of the physical therapy system during the second physical therapy session. The practitioner monitors the first channel and the second channel during the first time and the second time in order to coach, correct, and/or counsel the first patient and the second patient.

In another aspect, the present disclosure can include a method for facilitating the adaptation of telehealth for physical therapy. Steps of the method can be performed by a system comprising a processor and include conducting a unique first virtual physical therapy session for a first patient using a first instance of a physical therapy system at a time in a first channel, wherein a practitioner is at a location and the first patient conducts the unique first virtual physical therapy session from a first location remote from the location; and conducting a unique second virtual physical therapy appointment for a second patient using a second instance of the physical therapy system at the time in a second channel, wherein the practitioner is at the location and the second patient conducts the second unique second physical therapy session from a second location remote from the location. The practitioner monitors the first channel and the second channel during the time in order to coach, correct, and/or counsel the first patient and the second patient.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
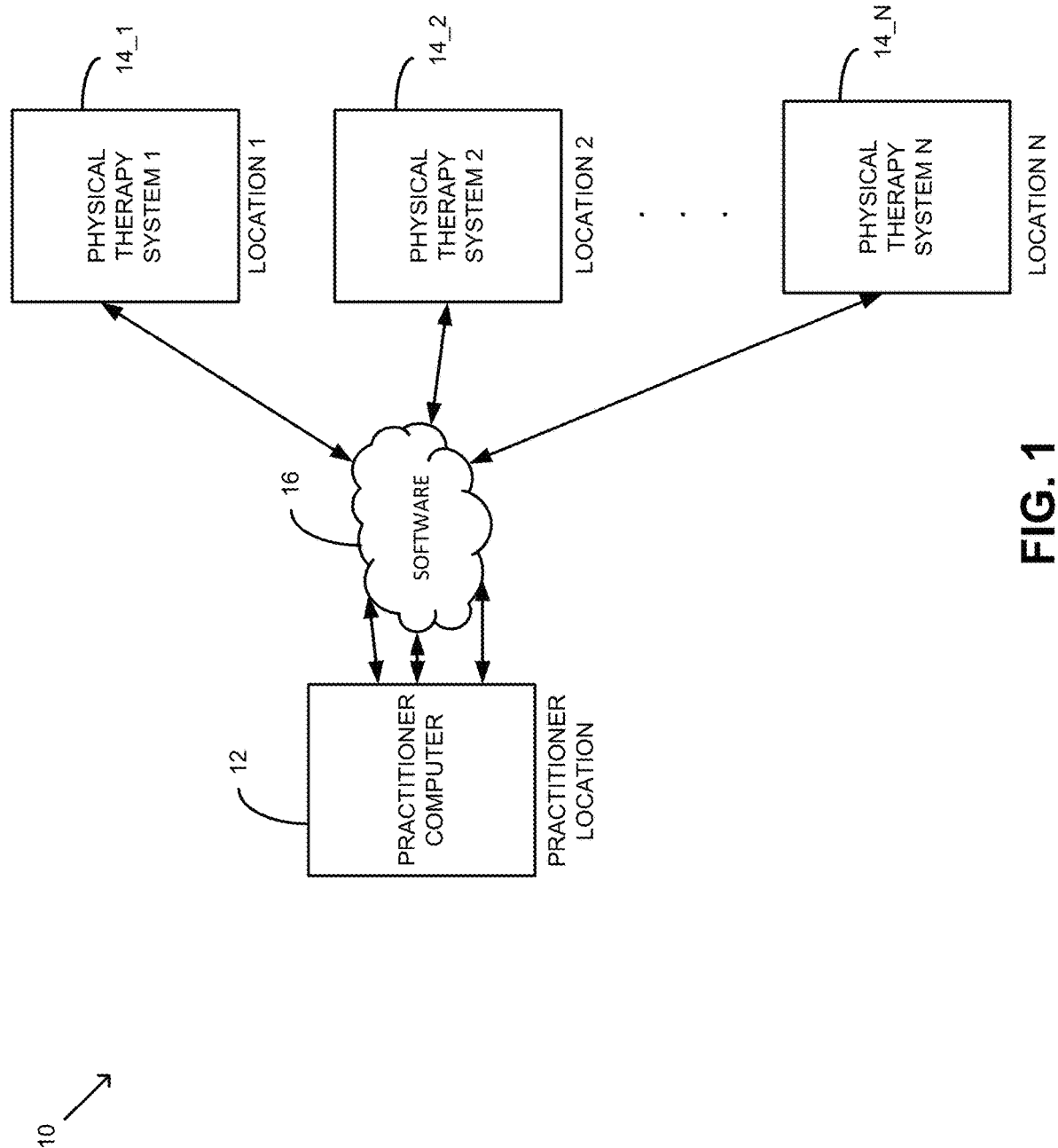
FIG. 1 is a diagram showing an example of a system that can facilitate the adaptation of telehealth in physical therapy.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "physical therapy" can refer to the treatment of an weakness by physical methods like exercise. The weakness can be an orthopedic weakness caused by disease, injury, deformity, age, surgery, or the like. Physical therapy can encompass exercise, athletics, athletic training, occupational therapy, physical therapy, or any treatment of a weakness by physical methods.

As used herein, the term "physical therapy session" can refer to a timed appointment for a patient to have physical therapy with the practitioner. The physical therapy session can be a virtual session where the patient is remote from the practitioner.

As used herein, the term "telehealth" can refer to the provision of healthcare, like physical therapy, remotely by means of telecommunications technology. For example, a unique, virtual physical therapy session can be conducted between a practitioner and a patient with a physical therapy system at a remote location.

As used herein, the term "code" can refer to a billing code for use with physical therapy.

As used herein, the term "channel" can refer to a line of communication set up between a practitioner and a patient so that the patient can send live video to the practitioner. The patient can establish a single channel with the practitioner. However, the practitioner can establish a plurality of channels to monitor a plurality of patients. As an example, the channel can have at least one-way audio and video capability so that the practitioner can see and hear the patient. The different channels cannot see or hear each other.

As used herein, the term "instance" can refer to an example or single use of something. For example, a first user can employ a first instance of a physical therapy system and a second user can employ a second instance of the physical therapy system, but both the first instance and the second instance can communicate with a same practitioner (although not simultaneously).

As used herein, the term "practitioner" can refer to an individual conducting the physical therapy session to coach, correct, and/or counsel a patient undergoing physical therapy. The terms "practitioner" and "provider" may be used interchangeably herein, but it should be noted that the term "provider" may include more than just the individual conducting the physical therapy session (e.g., at least a portion of a medical group, one or more providers, etc.).

As used herein, the term "N" can be used to represent any number greater than 2 and less than an infinite value (practically limited, for example, by the size of a computer memory and/or a practical ability of a practitioner). The term N is used herein to represent different numbers of elements (e.g., in FIGS. 1-14, for example, N patient physical therapy systems can correspond to a different number than N sensor (s)).

As used herein, the terms "subject" and "patient" can be used interchangeably and refer to any vertebrate organism. As an example, the subject or patient can be any human undergoing physical therapy.

As used herein, the term "sensor" can refer to a device that detects or measures a physical property and records, indicates, or otherwise responds to it. For example, the sensor can be an optical sensor. The optical sensor can be a camera, like a front-facing camera, such as within a tablet, a cellular phone, a 3-D optical sensor (e.g., LIDAR), or the like. As another example, the sensor can be a sticker-type sensor attachable on or near skin of a patient. The sticker-type sensor can be an inertial sensor, comprising an accelerometer, a gyroscope, a magnetometer, an optical sensor, a haptic motor, or the like.

II. Overview

Telehealth (remote healthcare services using electronic information and telecommunication technology) can be used by physical therapy practitioners to keep themselves and their patients safe. However, physical therapy practitioners have been slow to incorporate telehealth into their practices because of practical, regulatory and/or payor complexities. Described herein are systems and methods that facilitate the adaptation of telehealth in physical therapy. The systems and methods described herein can simplify the practical, regulatory, and/or payor complications for physical therapy practitioners.

Using the systems and methods described herein, the practitioner can schedule, conduct, and charge for multiple virtual physical therapy appointments in a practical manner that complies with regulations, such as those defined in the United States Health Insurance Portability and Accountability Act of 1996 (HIPAA), the European Union General Data Protection Regulation (GDPR), the United States personal health information/children's online privacy protection rules (PHI/COPPA), etc., and makes simplifies billing the payor for the virtual therapy session. Patients can be equipped with instances of a physical therapy system (the software and hardware are generally the same) that is set up at their location (each of which is remote from the practitioner) and the practitioner can have a computing device that includes a processor and/or a web application that can interface with the physical therapy systems. Using the schedule of the virtual physical therapy appointments, the practitioner can conduct unique virtual physical therapy sessions (that are HIPPAA, GDPR, PHI/COPPA, etc. compliant) with different patients, coaching, correcting, and/or counseling the individual patients. Notes and time stamps associated with the unique virtual physical therapy sessions can be associated with one or more billing codes to facilitate billing for the unique virtual physical therapy sessions.

III. System

One aspect of the present disclosure can include a system 10 (shown in FIG. 1) that can facilitate the adaptation of telehealth in physical therapy. Using the system 10, a physical therapy practitioner (referred to as "practitioner") can provide remote healthcare services to a plurality of patients in a manner that simplifyies practical, regulatory, and/or payor complications that have stopped practitioners from adopting telehealth into their practices. It should be noted that although the system 10 will be described as being used for telehealth applications, the system 10 can also be used for video appointments with practitioner/provider patient contact (e.g., to measure patient progress).

The practitioner can be at a location with the practitioner computer 12. The system 10 allows the practitioner to conduct multiple unique therapy sessions with multiple patients (e.g., two patients, three patients, four patients, five patients, six patients, seven patients, eight patients, nine patients, ten patients, etc.), each equipped with a unique instance of a physical therapy system 14_1-14_N, from the location (while ensuring privacy of the patients) using the practitioner computer 12. For example, the practitioner can conduct a unique first physical therapy session with a first patient at a first location at a time (using physical therapy system 1 14_1) and a unique second physical therapy session with a second patient at a second location at another time that overlaps the time (using physical therapy system 2 14_2). The two physical therapy systems 14_1, 14_2 can allow communication between the practitioner and the patients in a way that ensures patient privacy and confidentiality. For example, the practitioner can conduct the unique physical therapy sessions in different channels (by monitoring different sensors and/or front-facing cameras) that the practitioner can individually coach, correct, and/or counsel each of the first patient and the second patient during the unique physical therapy sessions. Telehealth allows the patients to rehabilitate by performing exercises designed by the practitioner without having the practitioner physically present with the patients; however, the system 10 allows the practitioner to "see" the patients during their appointments—both physically monitor their progress and see data related to their progress.

Notably, the system 10 solves practical problems by enabling the practitioner to see and schedule multiple telehealth visits simultaneously with higher connectedness via immediate objective data generated by one or more sensors (e.g., displayed on a dashboard visible to at least the practitioner). For example, the objective data can be related to the quality of exercises being performed, the number of reps, and the level of function of each patient on each exercise as well as the level of pain during each exercise. The system 10 adheres to regulatory aspects, such as those defined by the United States Health Insurance Portability and Accountability Act of 1996 (HIPAA), the European Union General Data Protection Regulation (GDPR), personal health information/children's online privacy protection rule (PHI/COPPA), etc., by maintaining privacy of each patient in the group since the practitioner can only be seen and/or heard by a specific patient so the other patients cannot hear/see the practitioner speaking to other patients. Additionally, the system 10 relieves payor complications by capturing billable events, enabling billing of each encounter with well-known billing codes.

With the system 10, a practitioner can use a practitioner computer 12 (e.g., laptop, desktop, tablet, smartphone, or the like) at a practitioner location and communicate with a plurality of patients at a plurality of locations (location 1—location N) remote from the practitioner location, each with a physical therapy system 14_1-14_N. In some instances, each patient can be equipped with an instance of the physical therapy system 14_1-14_N. The practitioner computer 12 and the physical therapy systems 14_1-14_N can communicate over a wide area network (e.g., the Internet, which may be secured through encrypted password protection) or a local area network.

The practitioner computer 12 and the physical therapy systems 14_1-14_N can each run uniquely enabled versions of software 16 (shown in a cloud on the network in FIG. 1). In some instances, the software 16 can be at least partially hosted by the practitioner computer 12 (acting as the master), while the physical therapy systems 14_1-14_N can act as slaves (only installing a portion of the software 15 on respective computers, which can be portable computing devices, such as a laptop, a tablet, a smartphone, or the like. In other instances, a server can be located at a remote location and host the software 16. The practitioner computer 12 and each of the physical therapy systems 14_1-14_N log into web-based versions of the software with different permissions. However, the software 16 may be hosted in any conceivable manner and is not to be limited by these examples.

The practitioner computer 12 and the physical therapy systems 14_1-14_N can run at least portions of the software 16 with different permissions enabled. For example, the software 16 with practitioner permissions (PR) is expressed as 16_PR. At least a portion of the features available in the software with practitioner permissions 16_PR are shown on the practitioner computer 12 in FIG. 2. As another example, the software 16 with patient permissions (PA) is expressed as 16_PA. At least a portion of the features available in the software with the patient permissions 16_PA are shown in FIG. 3.

Figure 2:
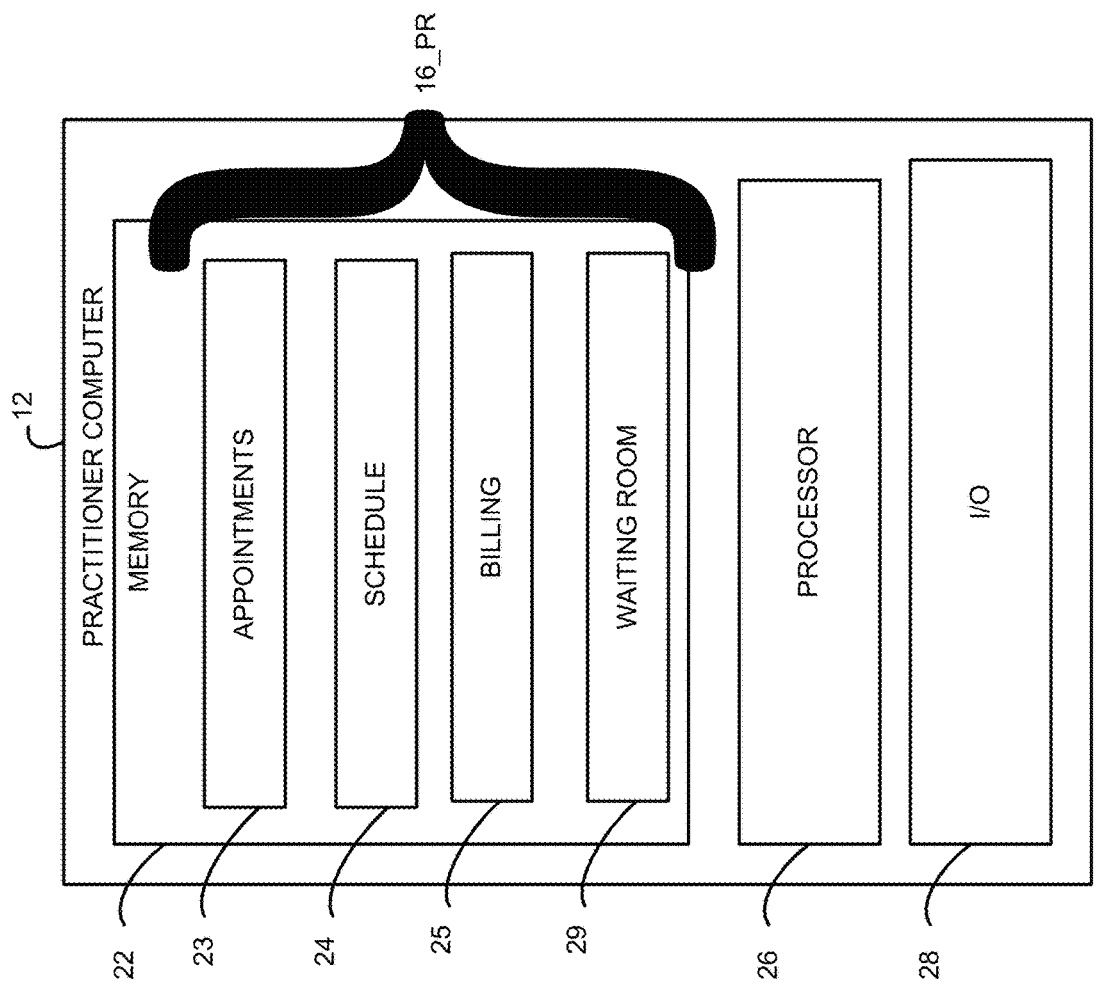
FIG. 2 is a diagram showing an example of a practitioner computer from FIG. 1 and associated software features.

As shown in FIG. 2, the practitioner computer 12 can have hardware including at least a memory 22, a processor 26, and at least one I/O device 28. Although shown as a single practitioner computer 12, at least a portion of the hardware components can be located remotely. For example, at least a portion of the memory 22 can be remote from the processor 26 and/or the I/O device 28. The memory 22 can be any type of non-transitory memory and may include one or more devices. The memory 22 can store computer-executable instructions that can be accessed and executed by the processor 26. The I/O device 28 can be one or more devices configured to allow inputs and outputs to/from the computer 12. Examples of such devices include, but are not limited to, a microphone, a speaker, a video recorder/player, a keyboard/touchscreen, speakers, or the like. The computer-executable instructions that can be stored in the memory 22 can include aspects of the software 16 that the practitioner has permissions for PR. Several example software routines that the practitioner can have permissions for 16_PR can include appointments 23, schedule 24, and billing 25. Although not illustrated, the practitioner computer 12 can also be configured to communicate across a public and/or private network according to wired and/or wireless protocols.

Figure 3:
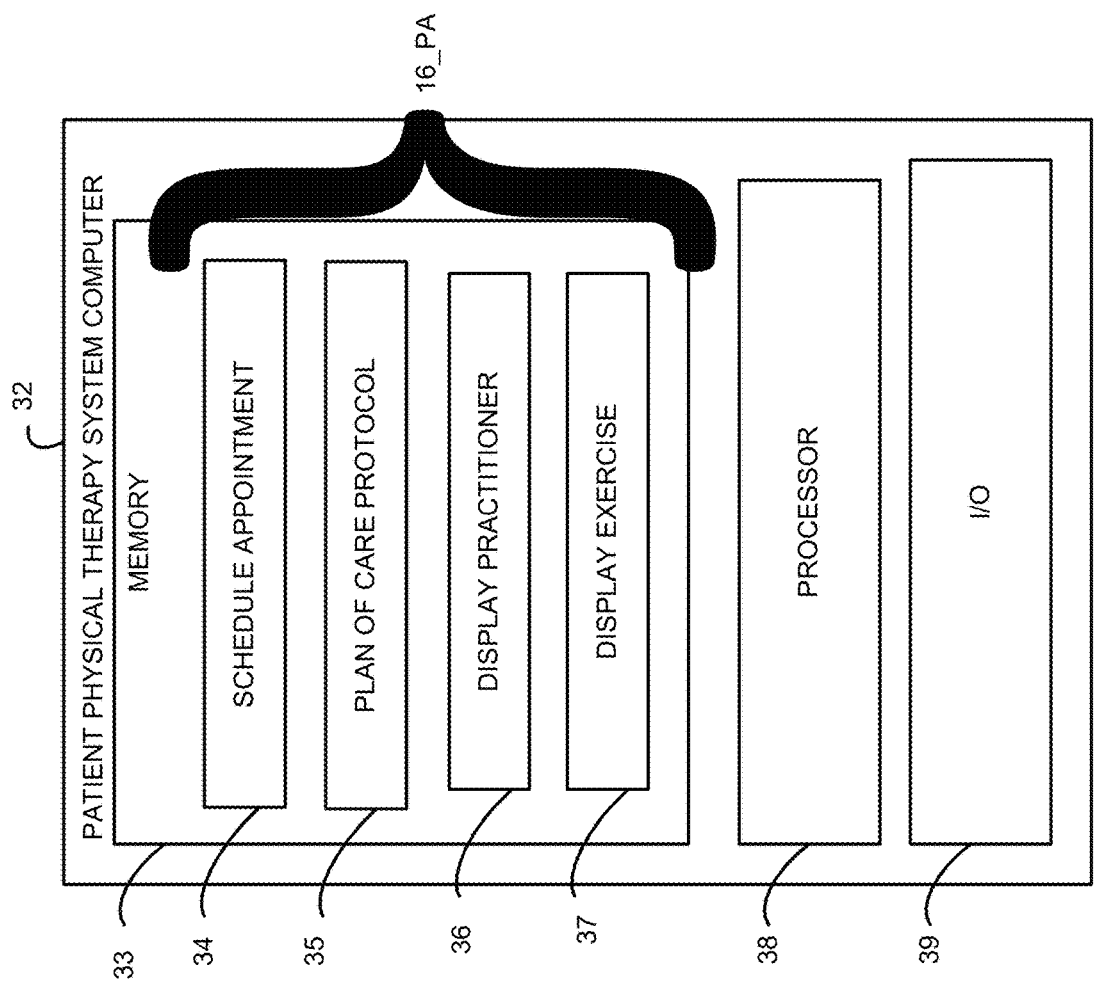
FIG. 3 is a diagram showing an example of a patient computer of the physical therapy system from FIG. 1 and associated software features.

As shown in FIG. 3, a patient physical therapy system computer 32 can be associated with the physical therapy system 14 (e.g., one of 14_1-14_N). The patient physical therapy system computer 32 may include a memory 33, a processor 38, and an I/O device 39 (similar in form to those found in the practitioner computer 12). Stored in the memory can be aspects of the software 16 that the patient can have permissions for PA. Several example software routines that the patient can have permissions for 16_PA can include schedule appointments 34 and the plan of care protocol 35 (that may be designed by a physician or other provider), display practitioner 36 and display exercise 37 (e.g., as a graphical representation that the patient can follow). Although not illustrated, the physical therapy system computer 32 can also be configured to communicate across a public and/or private network according to wired and/or wireless protocols.

Figure 4:
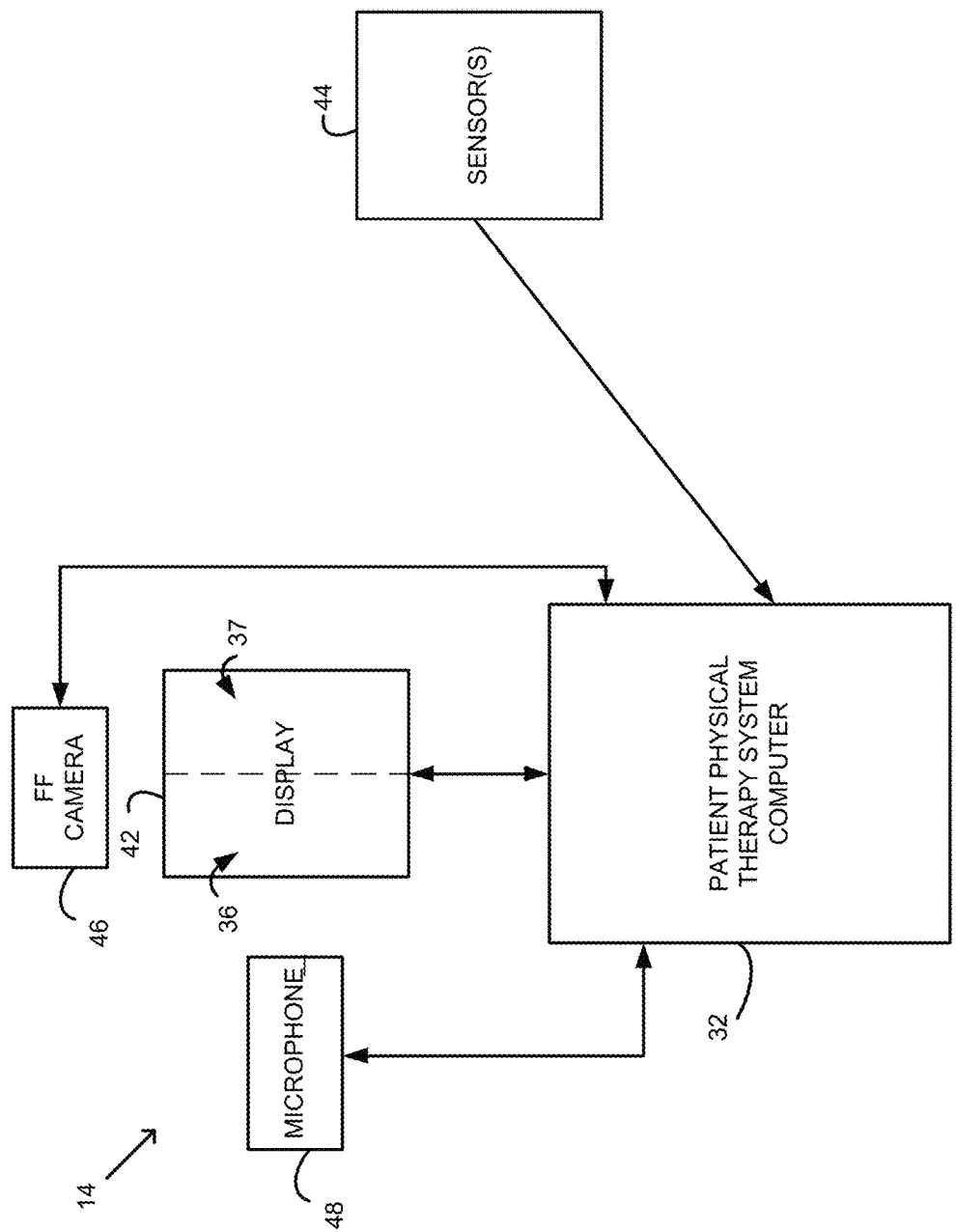
FIG. 4 is a diagram showing an example of an instance of a physical therapy system from FIG. 1.

In its basic form, the physical therapy system 14 can include the patient physical therapy system computer 32, a display 42 (that can display the practitioner 36 and/or display the exercise 37), one or more sensors 44 (configured to be placed/attached to specific locations on or near the patient), a forward facing (FF) camera 46 (to record images of the patient, in some instances, the FF camera 46 can be the one of the one or more sensors 44), which may be part of the physical therapy system computer 32, and a microphone 48 (or other audio capturing device) shown in FIG. 4. The display 42 can be included with the patient physical therapy system computer 32 or separate and distinct from the patient physical therapy system computer 32. For example, the physical therapy system computer 32 and the display 42 can be embodied as a tablet or a smartphone. In this example, through the tablet or smartphone, the software with patient permissions 16_PA can be installed as an app that may connect the patient with the practitioner and may receive inputs from the one or more sensors 44 (e.g., configured to be placed/attached on specific locations on the patient or near the patient), which can include objective data that can be provided to the practitioner so that the practitioner/provider can review progress and provide feedback to the patient in real time. The feedback can be related to whether exercises are being performed correctly and if adjustments are needed, whether the patient's pain is decreasing and the patient is progressing through the protocol appropriately whether a patient needs an in-office visit earlier than scheduled to address any concerns identified using the software 16_PA or 16_PR—before complications arise.

Figure 6:
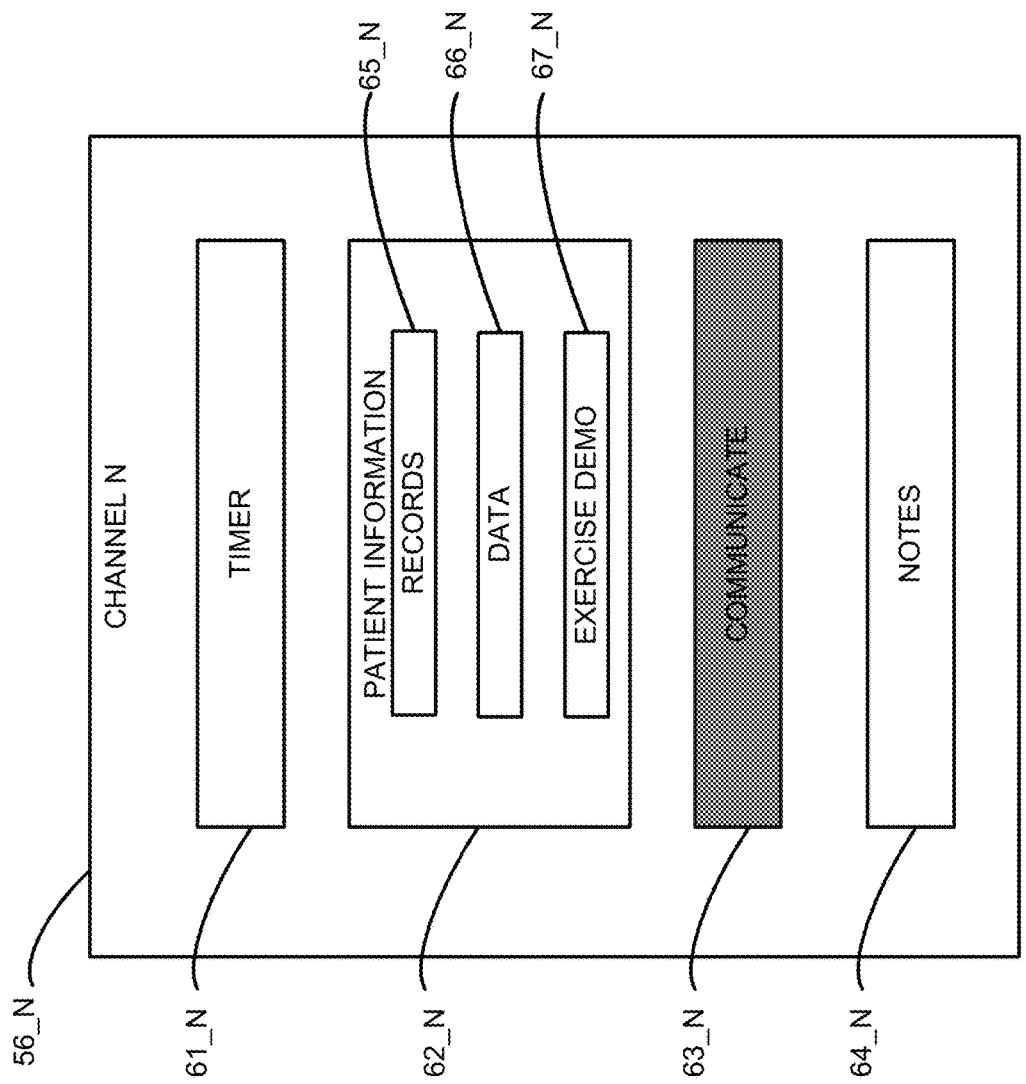
FIG. 6 is a diagram showing a detailed view of an example channel control software feature from FIG. 5.
Figure 7:
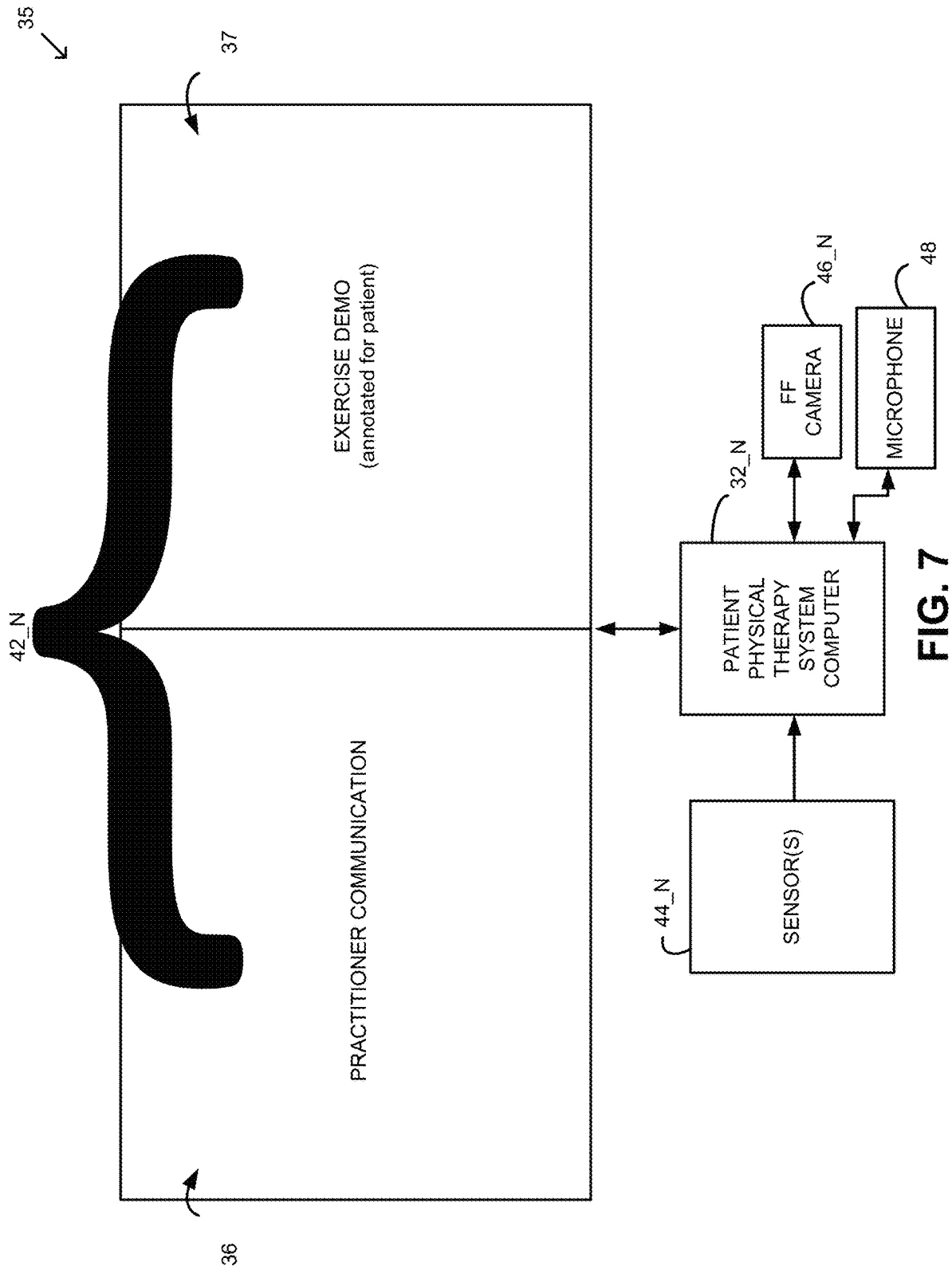
FIG. 7 is a diagram showing a detailed view of at least a portion of an example physical therapy system from FIG. 1 using the software features from FIG. 3 when the patient is contacted by the practitioner.

The software with practitioner permissions 16_PR and the patient permissions 16_PA can be configured by the practitioner to include a plan of care for the patient, which can also the practitioner to use exercises, determine the number of weeks or therapy, assign range of motion and resistance/repetition targets, record notes, billing codes (e.g., RPM codes), or the like. In some instances, the software with patient permissions 16_PA can be a slave to the software with practitioner permissions 16_PR, at least in some regards. Example executions of the example software routines that the practitioner has permissions for 16_PR, including appointments 23, schedule 24, and billing 25, are shown in FIGS. 5-6, 8, and 10, respectively. The practitioner may also have permissions 16_PR for a waiting room where patients who are not yet having an appointment can wait until it is time for their appointment and/or they are greeted by the practitioner. Similarly, example executions of the example software routines that the patient has permissions for 16_PA, including requesting and accepting appointments (scheduling appointments 34) and the plan of care protocol 35, are shown in FIGS. 7 and 9, respectively. In some instances, the software routines that the patient has permissions for 16_PA can be controlled, at least in part, by the software routines that the practitioner has permissions for 16_PR.

Figure 5:
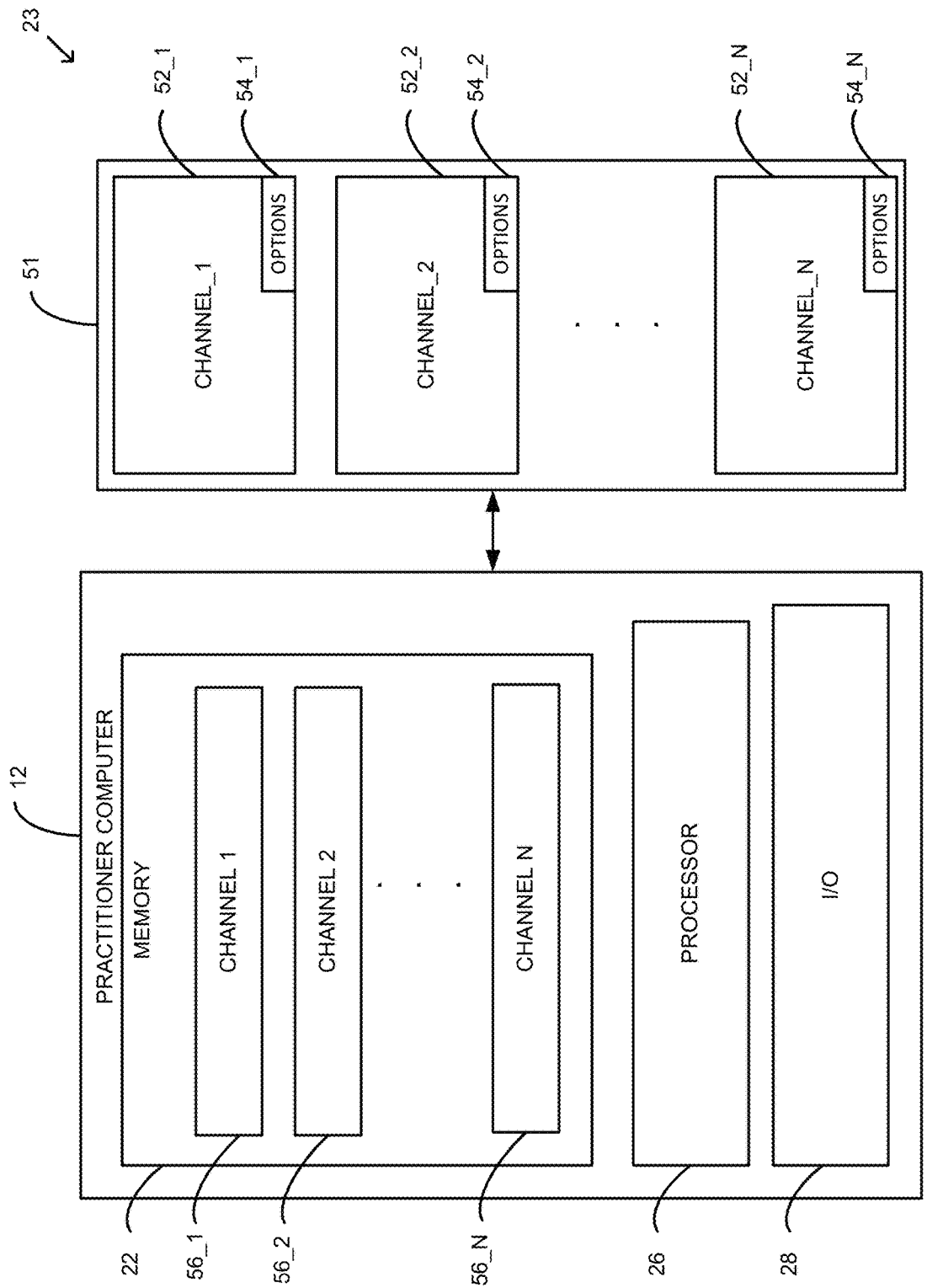
FIG. 5 is a diagram showing a detailed view of an example of the practitioner computer from FIG. 1 executing appointments using the software features from FIG. 2.

As shown in FIG. 5, the appointments 23 software routine can allow the practitioner to conduct multiple telehealth visits with multiple patients simultaneously. The different telehealth visits can be conducted on different channels, which can allow the practitioner to see (via the patients' front facing cameras) and hear each patient, but do not allow the patients to see or hear each other. For example, the practitioner can receive video from each of the different channels 52_1-52_N, which are each controllable by the practitioner (using channel controls 56_1-56_N). Privacy of each patient can be ensured because the other patients can be muted any time the practitioner speaks to one patient, for example.

The appointments 23 software routine can be stored in the memory 22 and executed by the processor 26 of the practitioner computer 12, which can have one or more I/O devices 28 and at least one display device 51. The at least one display device 51 can provide visualizations related to different therapy sessions on different channels (e.g., channel_1 52_1 with options 54_1-channel_N 52_N with options 54_N). The visualization can include one or more dashboard views. For example, the different channels 52_1-52_N can be displayed as a dashboard view. As another example, the different options 54_1-54_N within the channels 52_1-52_N can be displayed as one or more dashboard views. For example, the one or more dashboard views can include, for each patient, the quality of exercises being performed, the number of reps, and the level of function on each exercise, a level of pain caused by each exercise, or the like. One or more of the I/O devices 28 can be used to interact with the different therapy sessions on different channels (e.g., channel_1 52_1 with options 54_1-channel_N 52_N with options 54_N). In some instances, the different options 54_N can relate to different views related to the patient. For example, for each channel (e.g., channel_1 52_1-channel_N 52_N), the views can include an image of the patient, a graphic of an exercise associated with the patient, performance of the exercise associated with the patient, a dashboard view related to one or more aspects of the exercise associated with the patient and/or the exercise plan associated with the patient, or the like.

Each channel control (channel_1 56_1-channel_N 56_N) can be run as separate and distinct parts of the appointments software routine 23. An example of channel_N 56_N is shown in FIG. 6, although every channel can be similarly configured. As an example, the channel control for channel_N 56_N can have a timer 61_N, patient information 62_N (which can include records 65_N, data 66_N, and exercise demos 67_N), communicate 63_N. and notes 64_N. The timer 61_N can be used to establish the time of the appointment for the patient, as well as any additional intervention by the practitioner (which can be used for billing). The notes 64_N can also be used for billing if the practitioner makes any notes, the notes can be examined by the software and determined to indicate any billable events that happened during the appointment. The communicate 63_N can allow the practitioner to take over the patient's display to provide audio and/or video instruction to the patient, while muting the other patients (e.g., so that the other patients cannot see or hear the practitioner and the patient cannot see or hear the other patients).

The patient information 62_N can include records 65_N, data 66_N, and exercise demos 67_N. As an example, the patient information 62_N can also include information used for billing, like recorded video and/or transcripts of chats, messages written during the video call, etc. The records 65_N can include a patient record, which can include information about patient N, which can include current performance data, an exercise plan, information about the session, past performance data related to exercises done at previous appointments, medical records (e.g. patient cannot do a specific exercise due to weakness or injury), or the like-anything related to conducting the physical therapy session. The data 66_N can be current exercise results provided/generated by one or more sensors 44 (to provide immediate objective data) associated with the patient and may also include a live video of the patient performing the exercise. The exercise demos 67_N can include a 2D or 3D video simulation showing an animated figure demonstrating an exercise in the patient's plan of care. sometimes accompanied by verbal, written, or pictorial instructions to help the patient understand the exercise movements. The communication 63_N can allow the practitioner to speak and/or display video to the patient without the other patients seeing. The software can ensure that the patients do not see or hear each other's treatment, so when the practitioner is speaking with patient N, all other patients are muted and when the practitioner is on a video with patient N, no other video can be seen by patient N.

For example, the practitioner can notice that the patient is performing an exercise incorrectly (or sub-optimally) based on one or more aspects of the data 67_N. The practitioner can select one or the exercise demos 67_N and select the option to communicate 63_N with patient N. The practitioner computer 12 can still receive data from the other patients when communicating with patient N, but all vocal communication is muted so none of the patients can hear each other.

The practitioner can take over the display 42_N of the patient physical therapy session to communicate with the patient N. The patient physical therapy system computer 32_N can be linked to one or more sensors 44_N that can be associated with the patient to provide data related to the patient N and the forward facing (FF) camera 46 that provides images of the patient and a microphone 46 that provides audio related to the patient (and may also include a speaker that can allow the practitioner to speak to the patient). It should be noted that the FF camera 46 may be one of the sensors 44. The patient physical therapy system computer 32_N can also be linked to the display 42_N. Normally, the display 42_N can be linked to the exercise demo 37 (which can be annotated for the patient with information from the sensors 44_N). However, when the practitioner takes over the display 42_N, the practitioner can provide additional notations to the exercise demo 37 (or provide an alternative exercise demo showing an exercise that is easier or more difficult based on the data from the sensors 44_N). In some instances, an image of the practitioner 36 can appear on at least a portion of the display 42_N (it is shown in FIG. 7 as taking up half of the display, but can take up any portion from 0-100%). It should be noted that the size of the display and/or the images can vary with the device and, in some instances, can include a closed caption feature. The image of the practitioner 36 can allow the practitioner can individually coach, correct, and/or counsel patient N.

Figure 8:
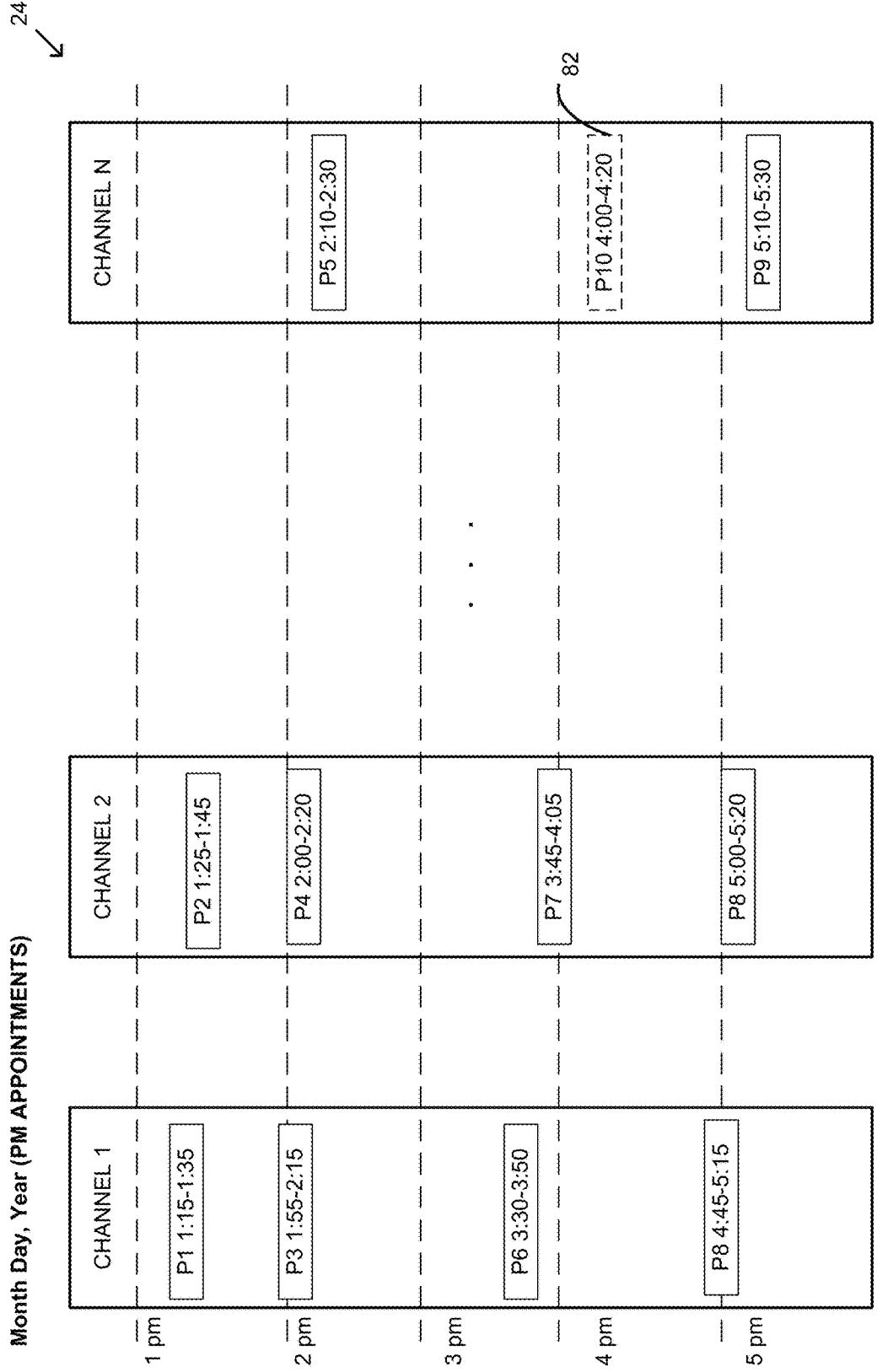
FIG. 8 is an illustration of an example schedule that can be created and used by the practitioner computer of FIG. 1 using the software features from FIG. 2.
Figure 9:
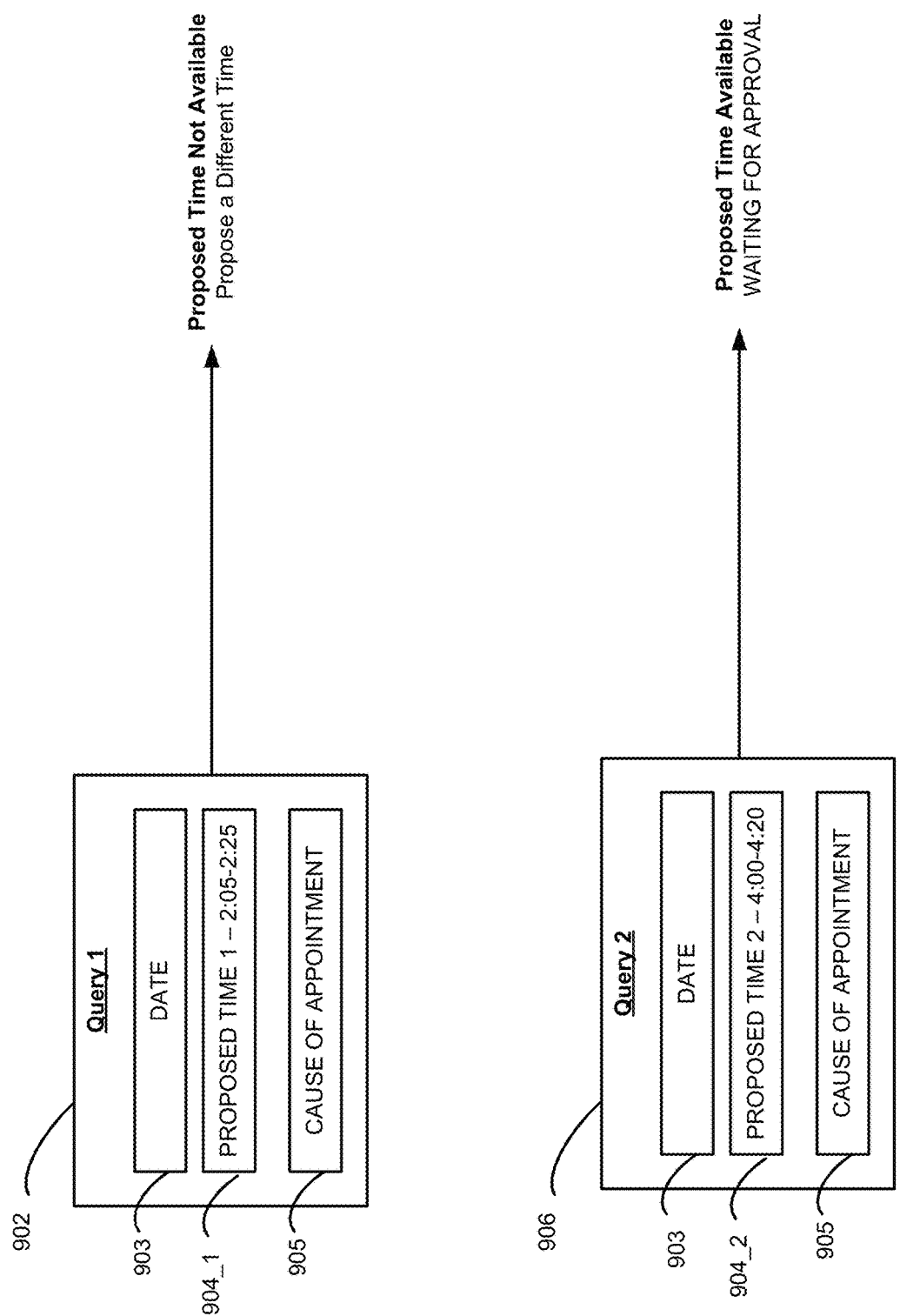
FIG. 9 is an illustration of an example schedule that can be used by a patient of FIG. 1 using the software features from FIG. 3.

An example afternoon schedule 24 for one day (Month Day, Year (PM APPOINTMENTS) is shown in FIG. 8. It should be noted that an encounter for P10 is tentatively scheduled for CHANNEL_N from 4:00-4:20, but has not yet been confirmed. Appointments with P1, P2, P3, P4, P5, P6, P7, P8, and P9 have been scheduled and confirmed. The appointments can each be set for a time period (e.g., as shown-20 minutes, but the time period can vary from, 5 minutes-1 hour, depending on billing conventions).

P10 can propose the appointment time using FIG. 9. P10 can send a query (Query 1 902) proposing a first date 903 and a first proposed time (PROPOSED TIME 1 904_1, with a correction for a time zone of the patient and/or the practitioner) with a cause of appointment 205. The patient physical therapy system 14 can consult the practitioner's schedule and send a message that the Proposed Time is Not Available, choose or propose a different time (or the message can propose different time(s) in which the practitioner has availability. P10 can send another query (Query 2 906) with a different proposed time (PROPOSED TIME 2 904_2, with a correction for a time zone of the patient and/or the practitioner), which is available. The patient physical therapy system 14 can place the appointment on the calendar 24 as awaiting approval.

Once the practitioner confirms the availability, a confirmation message can be sent to the patient and/or practitioner. One or more notifications can be sent to the patient and/or practitioner before the appointment (e.g., a week before, a day before, an hour before, 5 minutes before, etc., as often as selected by the patient and/or practitioner). In some instances, the practitioner can contact the patient for the appointment. In other instances, the patient can contact the practitioner for the appointment. In still other instances, the patient physical therapy system can remind the patient and/or the practitioner of the need for the appointment.

Figure 10:
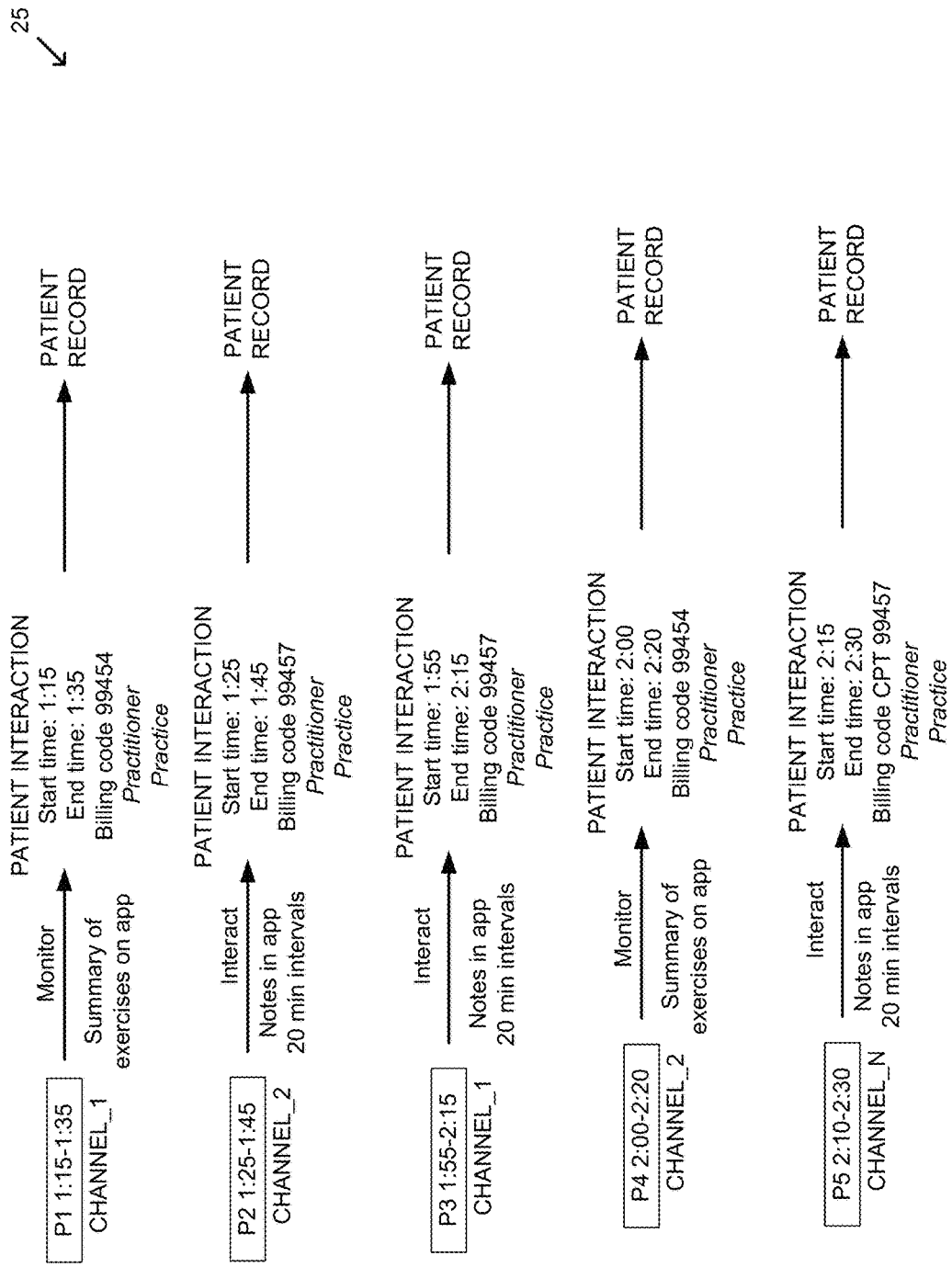
FIG. 10 is an illustration of an example of information that can be collected for future billing that can be done by practitioner computer of FIG. 1 using the software features from FIG. 2.

Each encounter between the patient and the practitioner can be billed, as shown in FIG. 10. The patient physical therapy system 14 can capture the billing instances for insurance reimbursement. For example, the stamps (recorded by the timer 61_N) can be used to track and determine which code to use. The time stamps can be associated with any type of interaction between the patient and the practitioner, including, for example email, text, phone call, in app messaging, and video chat. As shown in FIG. 10, the interactions can be monitor and interact (as noted, the interactions can be more varied, as long as they can be associated with a billing code). The billings can be associated with the individual patient record for future billing (e.g., to an insurance company).

IV. Methods

Another aspect of the present disclosure can include methods 110-150 as shown in FIGS. 11-15 for facilitating the adaptation of telehealth in physical therapy. The methods 110-150 can be performed by the system of FIG. 1, as shown and described further in FIGS. 2-9. For example, the methods 110-150 can be stored as program code within a non-transitory memory and executed by a processor.

The methods 110-150 are illustrated as a process flow diagram with flow chart illustrations. For purposes of simplicity, the methods are shown and described as being executed serially; however, it is to be understood and appreciated that the present disclosure is not limited by the illustrated order, as some steps could occur in different orders and/or concurrently with other steps shown and described herein. Moreover, not all illustrated aspects may be required to implement the methods.

Figure 11:
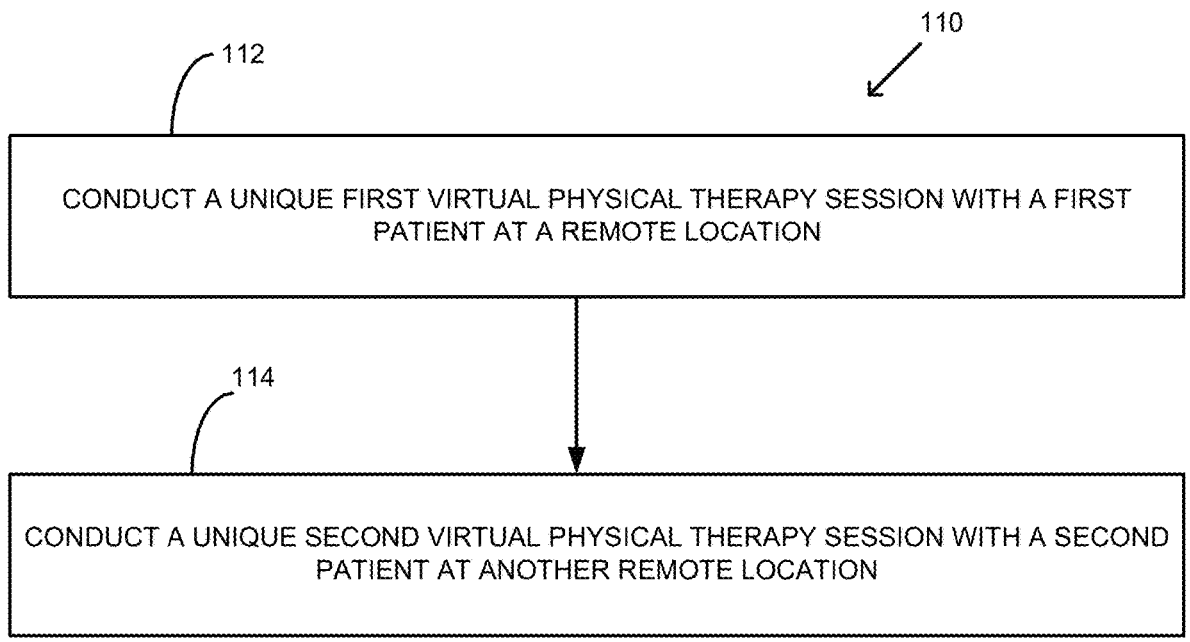
FIGS. 11 and 12 are process flow diagrams showing methods for facilitating the adaptation of telehealth in physical therapy.

Referring now to FIG. 11, illustrated is a method 110 for facilitating the adaptation of telehealth in physical therapy. At 112, a unique first virtual physical therapy session can be conducted (e.g., by a practitioner at a location) with a first patient at a remote location. The first patient can be equipped with an instance of a patient physical therapy system. At 114, a unique second virtual physical therapy session can be conducted (e.g., by the practitioner at the location) with a second patient at another remote location. The second patient can be equipped with another instance of a patient physical therapy system. The different unique physical therapy sessions can be conducted during overlapping times (such that the practitioner is watching both patients at the same time). It should be noted that the practitioner can conduct more than two unique virtual physical therapy sessions at once (e.g., three sessions, four sessions, five sessions, six sessions, seven sessions, eight sessions, nine sessions, ten sessions, etc.).

Figure 12:
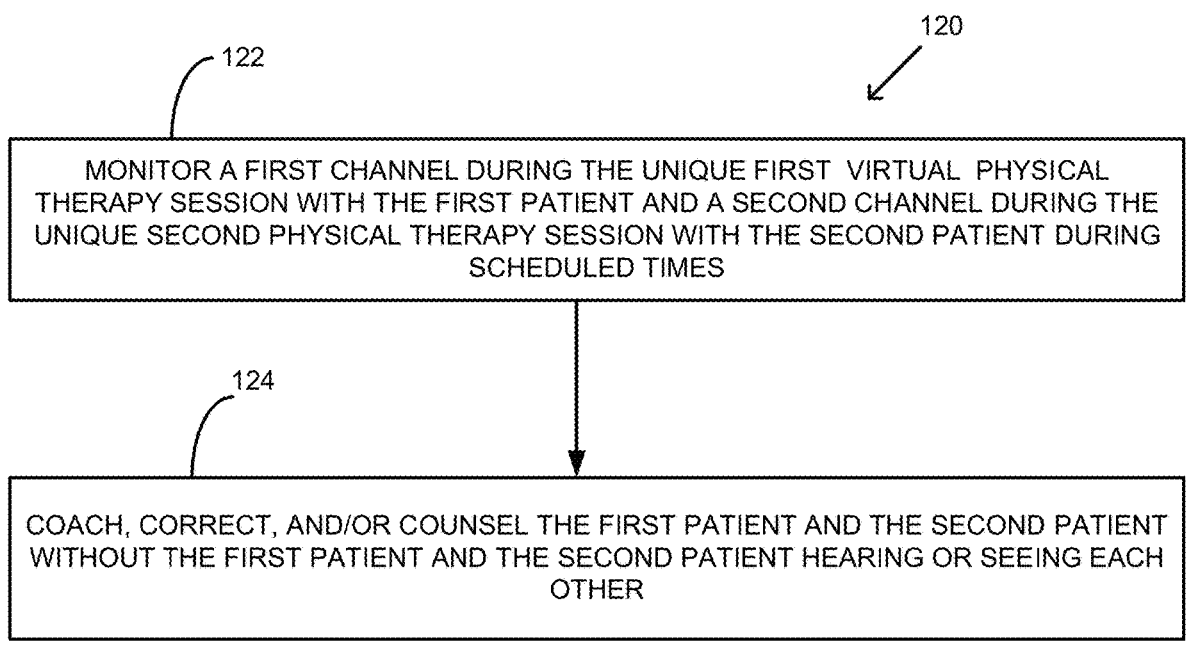

At shown in FIG. 12, method 120 relates to conducting the sessions established in FIG. 11. At 122, a first channel can be monitored during the unique first virtual physical therapy session with the first patient and a second channel can be monitored during the unique second virtual physical therapy session with the second patient during scheduled times (that at least partially overlap). The first channel and the second channel can make up at least a portion of a dashboard view viewable by the practitioner. At 124, the practitioner can coach, correct, and/or counsel the first patient and the second patient without the patients hearing or seeing each other. The system used by the practitioner can mute the other patient when the practitioner is talking to one of the first and second patient (ensuring patient privacy and security). For example, the coaching, correction, and/or counseling can be based on something seen in a video recording by a front-facing camera showing the patient (as seen in the different channels—different video recordings of different patients), based on audio from the patient, and/or based on data received from sensors associated with the patient.

Figure 13:
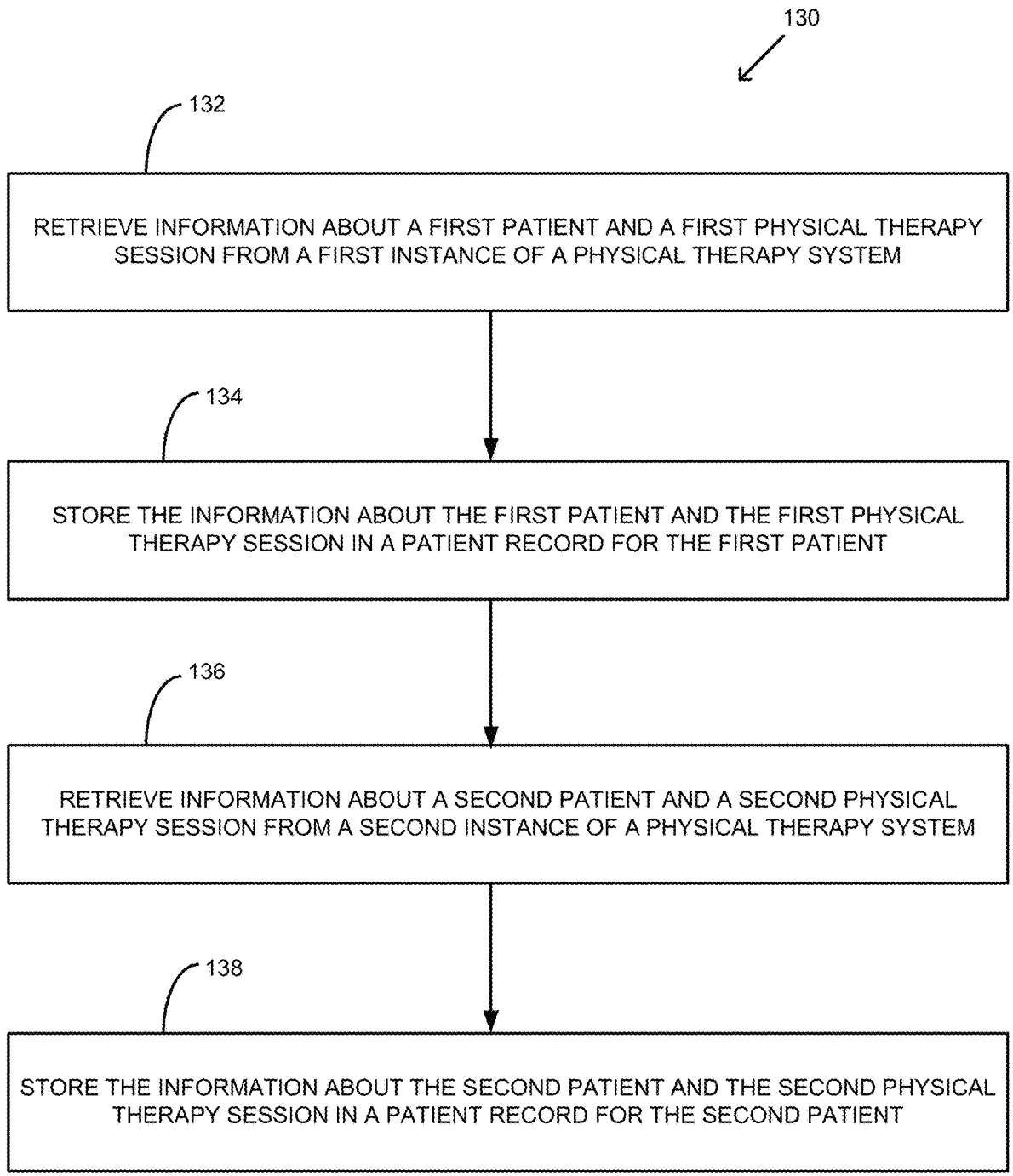
FIG. 13 is a process flow diagram showing a method for collecting data to facilitate future billing.

Referring now to FIG. 13, illustrated is a method 130 for collecting data to facilitate future billing. At 132, information about a first patient and a first physical therapy session can be retrieved from a first instance of a physical therapy system. At 134, the information about the first patient and the first physical therapy session can be stored in a patient record for the first patient. At 136, information about a second patient and a second physical therapy session can be retrieved from a second instance of a physical therapy system. At 138, the information about the second patient and the second physical therapy session can be stored in a patient record for the second patient.

Figure 14:
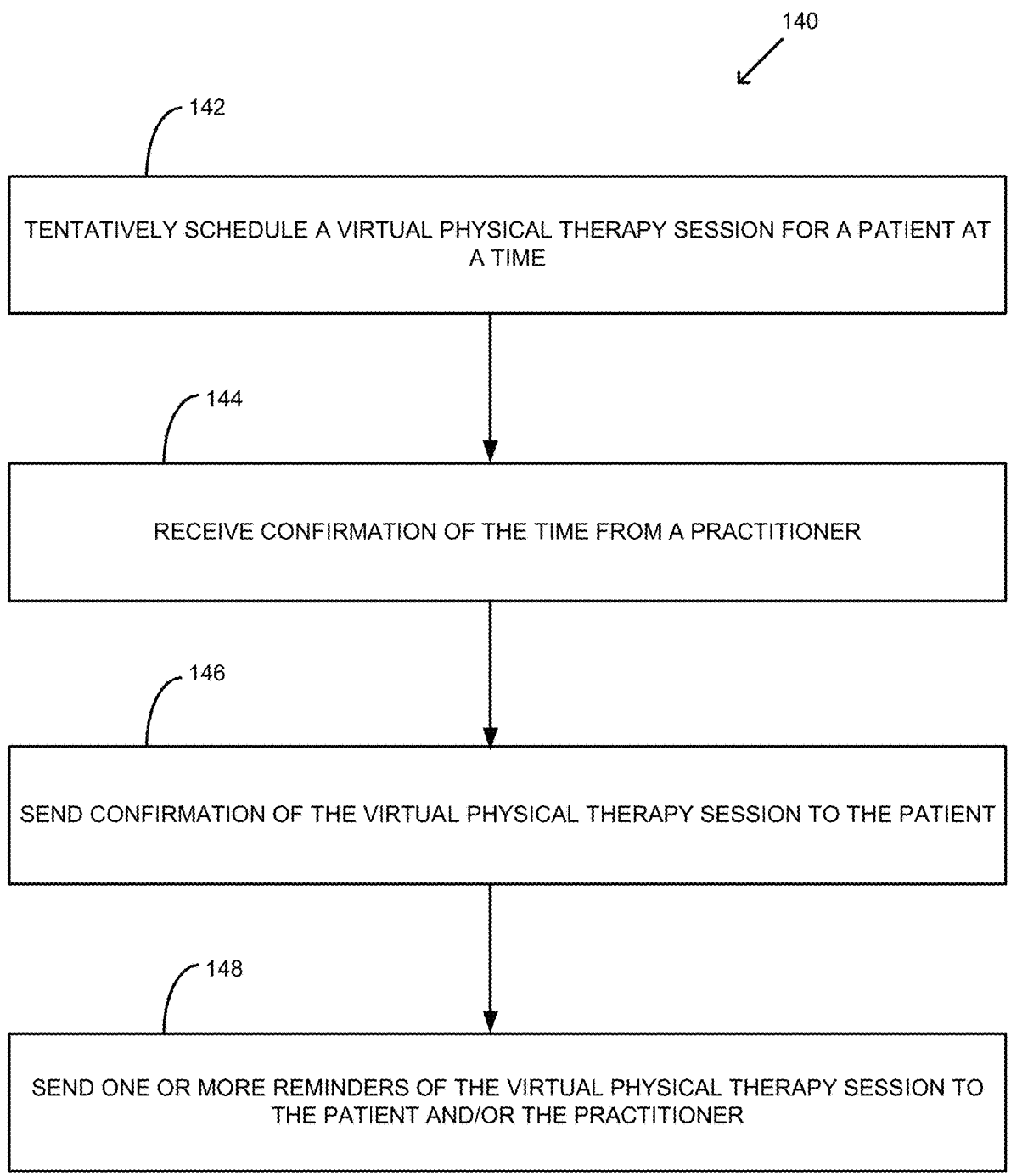
FIG. 14 is a process flow diagram showing a method for scheduling a virtual physical therapy appointment.

FIG. 14 illustrates a method 140 for scheduling a virtual physical therapy appointment. At 142, a virtual physical therapy session for a patient can be tentatively scheduled at a time by a physical therapy system (this can be true for any of the affiliated patients, like patient 1 or patient 2, for example, in response to a patient request, a practitioner request, a physical therapy system request, or the like). At 144, a confirmation of the time can be received from the practitioner. At 146, the confirmation of the physical therapy session can be sent to the patient. At 148, one or more reminders of the virtual physical therapy session can be sent to the patient and/or the practitioner (e.g., based on personalized settings).

Figure 15:
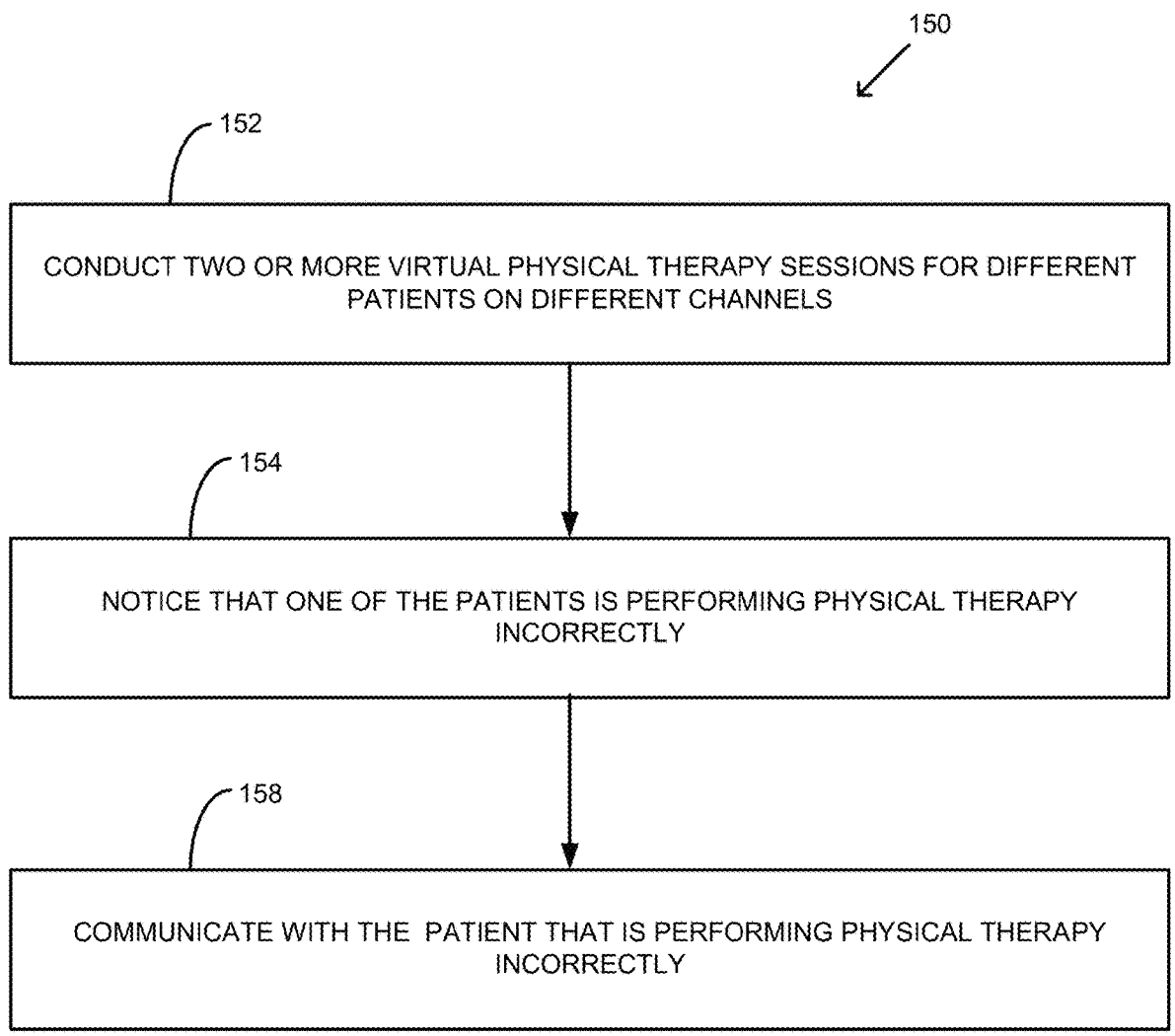
FIG. 15 is a process flow diagram showing a method for conducting multiple unique virtual physical therapy sessions.

Referring now to FIG. 15, illustrated is a method 150 for conducting multiple unique virtual physical therapy sessions. At 152, two or more virtual physical therapy sessions can be conducted for different patients on different channels. At 154, the practitioner can notice that one of the patients is performing an aspect of physical therapy incorrectly (e.g., from data and/or video). At 156, the practitioner can communicate (e.g., by video taking over at least a portion of a patient display) with the patient that is performing the physical therapy incorrectly. The other patients are muted from hearing the communication with the first patient by the software so that the patients cannot see or hear each other or another person's treatment.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A system comprising:
a first patient device at a first location, the first patient device comprising a forward facing camera and a microphone configured to record images and sounds of a first patient during a unique first physical therapy session;
a second patient device at a second location, the second patient device comprising a forward facing camera and a microphone configured to record images and sounds of a second patient during a unique second physical therapy session; and
a practitioner computer at a location unique from the first location and the second location, the practitioner computer comprising:
a memory storing instructions; and
a processor to access the memory and execute the instructions to:
conduct the unique first physical therapy session with the first patient using the first patient device by a practitioner at a time on a first channel, wherein the first patient uses a first instance of a physical therapy system with the first patient device during the first physical therapy session;
conduct the unique second physical therapy session with the second patient using the second patient device by the practitioner at another time on a second channel, wherein the other time overlaps the time, wherein the second patient uses a second instance of the physical therapy system with the second patient device during the second physical therapy session,
enable the practitioner to remotely monitor the unique first physical therapy session and the unique second physical therapy session in order to coach, correct, and/or counsel the first patient and the second patient during overlapping times;
during overlapping time, the practitioner computer switches between the unique first physical therapy session and the second physical therapy session by:
determine an active channel and a non-active channel from the first channel and the second channel based on whether the practitioner is speaking to the first patient on the first channel or to the second patient on the second channel,
mute the non-active channel, wherein the practitioner computer collects data from both the first channel and the second channel, and
over take the first patient device or the second patient device associated with the active channel so the practitioner is able to communicate with the first patient or the second patient, respectively;
record notes made by the practitioner about the unique first physical therapy session on the first channel and/or about the unique second physical therapy session the second channel;
record time stamps associated with the unique first physical therapy session and time stamps associated with the unique second physical therapy session, wherein the time stamps establish the time of an appointment and any intervention by the practitioner; and
capture billing instances for the unique first physical therapy session and for the unique second physical therapy session based on the collected data, notes made by the practitioner, and time stamps associated with the unique first physical therapy session and the unique second physical therapy session, respectively.

2. The system of claim 1, wherein three or more unique physical therapy sessions are conducted at overlapping times on three or more unique channels.

3. The system of claim 1, wherein the processor executes the instructions to store information about the first patient and the first physical therapy session provided by the first instance of the physical therapy system in a patient record for the first patient and to store information about the second patient and the second physical therapy session provided by the second instance of the physical therapy system in a patient record for the second patient.

4. The system of claim 1, the processor further executes instructions to:
schedule the first unique physical therapy session at the first time based on a first request and the second unique physical therapy session at the second time based on a second request, wherein the first time and the second time overlap; and
provide one or more reminders of the first unique therapy session to the first patient and/or the practitioner and one or more reminders of the second unique physical therapy session are provided to the second patient and/or the practitioner.

5. The system of claim 1, wherein the practitioner computer further comprises an input/output device and a display configured to enable the practitioner to view and communicate via video.

6. The system of claim 1, wherein the processor further executes instructions to notify the practitioner before a start time of the first physical therapy session and a start time of the second physical therapy session.

7. The system of claim 1, wherein the processor is further executes instructions to receive the recorded images and sounds of the first patient during the unique first physical therapy session and of the second patient during the unique second physical therapy session, respectively, wherein practitioner monitors the recorded images and sounds of the first patient in the first channel and the front facing camera of the second patient in the second channel.

8. The system of claim 7, wherein the practitioner monitors an exercise of the first patient and another exercise of the second patient and the processor is further configured to execute instructions to receive data from at least one sensor related to performance of the exercise of the first patient from the first instance of the physical therapy system and the other exercise of the second patient from the second instance of the physical therapy system.

9. The system of claim 1, wherein the processor is further configured to execute instruction to send messages to the first patient and the second patient confirming appointments with the practitioner.

10. The system of claim 1, wherein the practitioner computer further comprises a display device and the processor is further configured to execute instructions to display a dashboard view comprising a visualization associated with the first channel and a visualization associated with the second channel, wherein the visualizations comprise at least one of the quality of an exercise being performed, a number of reps, a level of function of the exercise, a level of pain caused by the exercise, an image of the patient, and a graphic of the exercise.

11. A method comprising:
connecting, using a practitioner computer comprising a processor, a system comprising:
the practitioner computer,
a first patient device at a first location, the first patient device comprising a forward facing camera and a microphone configured to record images and sounds of a first patient during a unique first physical therapy session, and
a second patient device at a second location, the second patient device comprising a forward facing camera and a microphone configured to record images and sounds of a second patient during a unique second physical therapy session, wherein the practitioner computer is at a location unique from the first location and the second location;
conducting, using the system, the unique first virtual physical therapy session for the first patient using a first instance of a physical therapy system with the first patient device at a time in a first channel;
conducting, using the system, a unique second virtual physical therapy appointment for the second patient using a second instance of the physical therapy system with the second patient device at another time in a second channel, wherein the other time overlaps with the time;
enabling, using the system, the practitioner to remotely monitor the first channel and the second channel in order to coach, correct, and/or counsel the first patient and the second patient during the overlapping times;
during overlapping times switching, using the system, the practitioner's computer between the unique first physical therapy session and the unique second physical therapy session by:
determining, by the system, an active channel and a non-active channel from the first channel and the second channel based on whether the practitioner is speaking to the first patient on the first channel or to the second patient on the second channel,
muting, by the system, the non-active channel, wherein the practitioner computer collects data from both the first channel and the second channel, and
over taking, by the system, the first patient device or the second patient device associated with the active channel so the practitioner is able to communicate with the first patient or the second patient, respectively;
recording, by the system, time stamps associated with the unique first physical therapy session and time stamps associated with the unique second physical therapy session, wherein the time stamps establish the time of an appointment and any intervention by the practitioner; and
capturing, by the system, billing instances for the unique first physical therapy session and for the unique second physical therapy session based on the collected data, notes made by the practitioner, and time stamps associated with the unique first physical therapy session and the unique second physical therapy session, respectively.

12. The method of claim 11, further comprising conducting, using the system, three or more unique physical therapy sessions at the time on three or more unique channels.

13. The method of claim 11, further comprising storing, by the system, information about the first patient and the first physical therapy session from the first instance of the physical therapy system in a patient record for the first patient and information about the second patient and the second physical therapy session from the second instance of the physical therapy system in a patient record for the second patient.

14. The method of claim 11, further comprising scheduling the first unique virtual physical therapy session at the first time based on a first request and the second unique virtual physical therapy session at the second time based on a second request, wherein the first time and the second time overlap,
wherein reminders of the first unique virtual therapy session are provided to the first patient and/or the practitioner and reminders of the second unique physical therapy session are provided to the second patient and/or the practitioner.

15. The method of claim 11, wherein the unique first physical therapy session and the unique second physical therapy session comprise the practitioner communicating with video.

16. The method of claim 11, further comprising displaying, by the system, a dashboard view on the practitioner computer comprising a visualization associated with the first channel and the second channel, wherein the visualizations comprise at least one of the quality of an exercise being performed, a number of reps, a level of function of the exercise, a level of pain caused by the exercise, an image of the patient, and a graphic of the exercise.

\* \* \* \* \*